United States Patent [19]

Koutavas

[11] Patent Number: 5,672,055

[45] Date of Patent: Sep. 30, 1997

[54] DENTAL ARTICULATOR AND METHOD

[76] Inventor: Ioannis Koutavas, 5-9 Vapheiochoriou Street, GR-114 76 Athens, Greece

[21] Appl. No.: 582,387

[22] Filed: Jan. 3, 1996

Related U.S. Application Data

[60] Division of Ser. No. 331,937, Oct. 31, 1994, Pat. No. 5,531,595, which is a continuation-in-part of Ser. No. 50,070, filed as PCT/GR92/00007, Jun. 10, 1992, Pat. No. 5,380,199.

[30] Foreign Application Priority Data

Jul. 17, 1991 [GR] Greece ........................ 910100316

[51] Int. Cl.$^6$ .................................................. A61C 11/00
[52] U.S. Cl. ................................................... 433/60
[58] Field of Search ............................. 433/58, 60, 62, 433/65

[56] References Cited

U.S. PATENT DOCUMENTS

| | | | |
|---|---|---|---|
| 4,175,325 | 11/1979 | Beckwith | 433/60 |
| 4,412,822 | 11/1983 | Blechner | 433/60 |
| 4,496,320 | 1/1985 | Hwang et al. | 433/60 |
| 5,026,282 | 6/1991 | Koike | 433/62 |
| 5,076,786 | 12/1991 | Callne | 433/60 |
| 5,352,117 | 10/1994 | Silva | 433/60 |
| 5,494,440 | 2/1996 | Silva et al. | 433/58 |
| 5,506,095 | 4/1996 | Callne | 433/34 |

*Primary Examiner*—Nicholas D. Lucchesi
*Attorney, Agent, or Firm*—Herbert Dubno

[57] ABSTRACT

A method of determining the position of an upper jaw cast and a lower jaw cast using a dental articulator provides a disposable plastic holder in the lower jaw cast and mounts it in a metal bracket bar fitted to the base of the articulator whose telescoping post allows adjustment of the height of the head above the base. A bracket bar mounted on the head and spring biased so that this bracket bar can move in a plane and can pivot about a horizontal axis receives another plastic disposable holder which can fit into a cavity in the upper casting. Once the castings are properly positioned, a hard-enable composition can be cast into the recess to embed the holder in the upper casting.

2 Claims, 10 Drawing Sheets

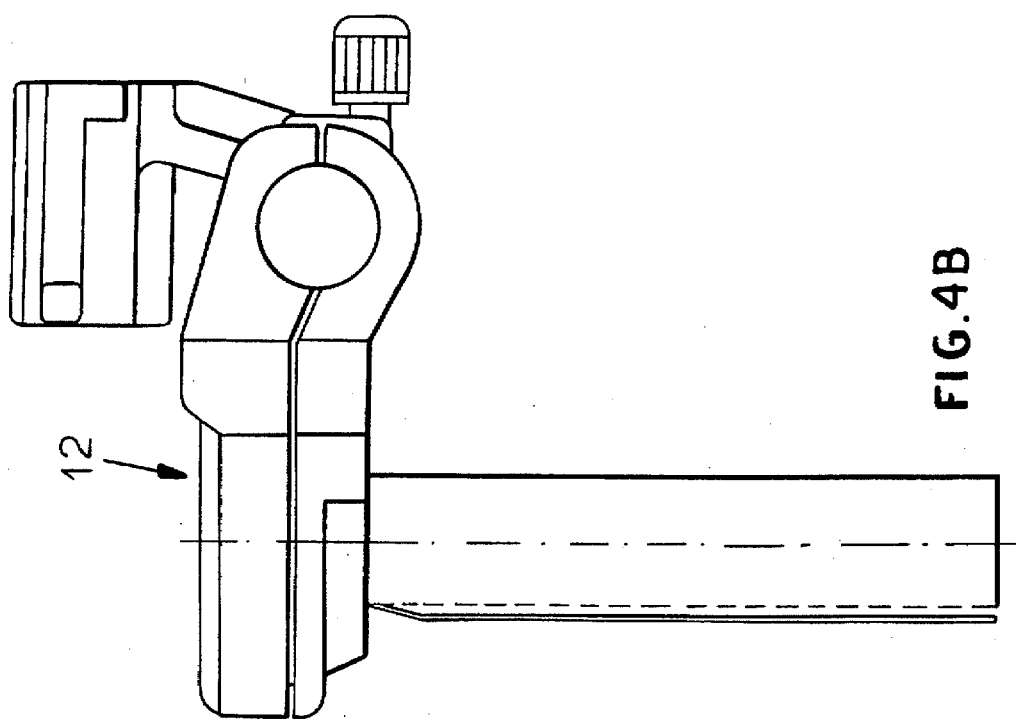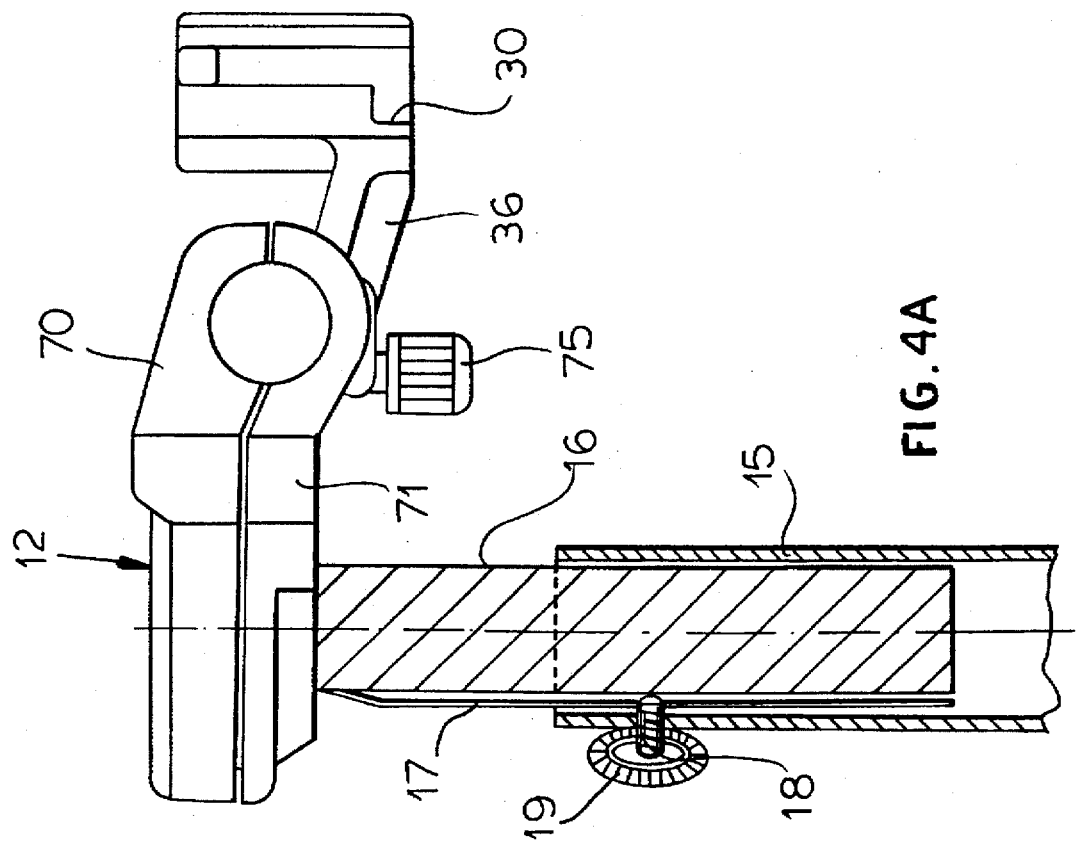

DENTAL ARTICULATOR AND METHOD

CROSS REFERENCE TO RELATED APPLICATIONS

This application is a division of Ser. No. 08/331,937, filed Oct. 31, 1994, now U.S. Pat. No. 5,531,595 which is a continuation-in-part of application Ser. No. 08/050,070 filed 27 Apr. 1993 and now U.S. Pat. No. 5,380,199. Application Ser. No. 08/050,070 is a national phase of PCT/GR 92/00007 filed 10 Jun. 1992 and based, in turn, upon a national application 91 01 00316 filed 17 Jul. 1991 in Greece under the international Convention. The benefit of these earlier applications is claimed pursuant to 35 USC 119 and 35 USC 120.

FIELD OF THE INVENTION

My present invention relates to a dental articulator to be used in the mounting, fabrication and adjustment of dental casts in a dental prosthesis laboratory and to a dental articulation method.

More particularly the invention relates to a so-called plane line dental articulator.

BACKGROUND OF THE INVENTION

Plane line dental articulators can provide for the mounting of dental casts with or without gypsum (plaster). The articulators can simulate the movements of the lower jaw relative to the upper jaw on the articulator, an action which does not normally match the functioning of these parts in the oral cavity. With existing apparatus of this type, adjustment is limited, especially to the height of the dental cast.

Earlier articulators for the purposes described have had disadvantages resulting from, for example, the sensitivity to dimensional changes in the plaster used in cast mounting but this can cause distortion of the articulation because of the fact that the articulator cannot be adjusted with relation to the height of the dental casts. The articulator is also difficult to handle since the user must hold the articulator frame together with the mounted casts during prosthodontic work.

Removal of the casts from the articulator is carried out by breaking the plaster which can jeopardize the integrity of the cast and damage the articulator. Because the casts in many cases are mounted directly on a metal frame, the articulator generally is applicable only to a single use.

With articulators which do not mount the casts with plaster, the mounting of the cast is time-consuming because of the nature of the molding process used and the manner in which the cast must be manipulated.

In many instances with this second type of articulator, the cast mounting is not sufficiently firm and the accuracy of the prosthetic work is jeopardized. The versatility of the system is greatly limited.

These drawbacks were overcome by the apparatus described in application Set. No. 08/050,070, in which a base is connected by a post to a head and both the base and the post were provided with bars having dovetail grooves in which dovetail formations of the member engaged in the cast could be received.

According to that system, to secure accurate movements on the articulator and the harmonization thereof with the normal movements of the lower jaw, the articulator provided a new system located on the lower element of the articulator which executes the movements while making available the upper element of the articulator for the same movements of the lower jaw.

A sleeve stopper and holder has a treble function by which the dental articulator can be applied to cases of cast mounting with or without gypsum (plaster).

My earlier articulator offered a solution to the problem of adjusting the articulator with relation to the height of the cast by providing a vertical guide meant for the vertical movement of the upper element of the articulator which can be adjusted depending on the height of the dental cast.

The mounting of the dental casts on the articulator by means of plaster was carried out on the disposable rubber sleeve-stopper and not directly on the metallic frame, thereby facilitating the removal and exact remounting of the casts thereon.

The use of the sleeve-stoppers prevented the plaster from dimensional change because the stoppers, which were rubber pins built into the sleeve-stoppers, come into direct contact with the casts which they support during their mounting on the articulator and limit to a minimum any dimensional change. The stoppers also functioned as guiding points determining the even or uniform plaster quantity used for the mounting of the casts on the upper and lower jaw.

OBJECTS OF THE INVENTION

It is, therefore, the principal object of the present invention to provide an improved articulator which extends the principles of my earlier articulator and further improves upon that apparatus.

It is also an object of the invention to provide an improved method of positioning the dental cast utilizing the more advanced articulator.

Another object of the invention is to provide a more versatile dental articulator which can be used for dental casts of various heights with varying degrees of adjustability.

Still another object of the invention is to provide an improved dental articulator which is free from drawbacks which have characterized earlier articulators.

SUMMARY OF THE INVENTION

These objects and others which will become apparent hereinafter are attained, in accordance with the invention, in a dental articulator which basically comprises a base adapted to rest upon a horizontal surface or table, a telescoping post extending upwardly from the base and a head mounted on the post and vertically adjustable therewith relative to the base.

According to the present invention, adapted to be embedded in the cast for the lower jaw and the cast for the upper jaw are disposable holders having openwork tongues which project into the respective casts and extend from plates configured to slide vertically into respective brackets projecting from the base and head, respectively, and adapted to be locked in place thereon.

According to a method aspect of the invention, the holder for the lower jaw cast is embedded therein and that holder is then mounted on the bar of the bracket engaged in the base while the holder for the upper jaw cast is mounted on the head of the articulator and the upper jaw cast is formed with an upwardly open recess in which the tongue of the latter holder is engaged once the upper jaw cast has been properly positioned on the lower jaw cast. Plaster or some other hardenable composition is then cast around the tongue and this holder into the recess to bond the upper jaw cast to the tongue of the disposable holder previously fitted to the head of the articulator.

According to a feature of the invention, the holders are composed of a disposable plastic which is relatively stiff, the holder being shaped to allow a certain resilient engagement with the bracket bar, the head or base, respectively. In particular, these bars may be provided with a plurality of spaced-apart upstanding formations which are receivable in respective recesses in the plate of the respective holders, at least outer tongues of which can be resiliently displaced by these formations to ensure a snug engagement of the holder on the respective bracket bar.

The upper bracket bar is advantageously connected to the head by a rearwardly extending lug which, within the head, is connected to a transverse pin, the latter being capable of pivoting about its horizontal axis within the head between a pair of screws which can shift the pin to one side or the other side of a vertical median plane through the articulator and can lock the pin between them. The pin can be engaged, in addition, by a pair of springs which can be compressed by movement of the pin within the head and the bracket bar further toward the head, the springs biasing the bracket bar toward the median position upon angular displacement of the bracket bar about a vertical axis perpendicular to the pin axis.

The lug, moreover, may be provided with a screw which can brace against the housing of the head to adjust the inclination of the holder about the pin axis.

According to one aspect of the invention, the bracket bar for the holder of the lower jaw cast may be fixed on the base. In that embodiment, the holder bar may form one piece with the casting of the base and the outer member of the telescoping post which can have a setscrew locking the vertical position of the inner member of that post.

Alternatively, where movement of the lower jaw casting is desired, the base can be hollow and the lower bracket bar can have its lug extending into the interior of the hollow base through a window opening at the front side thereof. That lug may be formed with a pair of pins within the interior of the base and to which respective tension springs are anchored to draw the resiliently biased lug inwardly and into a median position. The lug can have a pin which projects into a recess limiting the displacement of that lug. The recess in turn can be formed in the cast housing or, if desired, in the cover plate for the base.

The springs in turn can be anchored on pins fixed in the base.

It has been found to be advantageous, moreover, to provide the bracket bar with protrusions which can be engaged between projections on the front of the base.

To lock the lug and hence the lower holder in its adjusted position, the base may be provided with a locking screw engageable with the lug in its displaced position.

The apparatus forming the dental articulator set of the present invention also includes a mold for the upper jaw casting which, in use, will leave the aforementioned recess in that casting, open rearwardly and adapted to receive the tongue of the respective holder. The tongues of the upper and lower holders are of openwork construction so that the plaster can extend into the tongue as well as encase it.

The method of the invention can comprise the steps of:
(a) casting into a lower jaw cast a tongue of a disposable preformed lower plastic holder having a plurality of formations along a plate of the holder from which the tongue projects;
(b) casting an upper jaw cast with an upwardly and rearwardly open recess;
(c) mounting the lower jaw cast upon a lower metal bracket bar of a dental articulator by sliding the plate of the lower holder over mating formations on the lower metal bracket bar;
(d) mounting on an upper metal bracket bar of the dental articulator a disposable preformed upper plastic holder having a plurality of formations along a plate of the upper holder from which another tongue projects;
(e) positioning the upper jaw cast above the lower jaw cast and in alignment therewith while receiving the other tongue in the recess; and
(f) thereafter filling the recess with a hardenable material to embed the other tongue therein and hardening the material to anchor the upper jaw cast to the upper holder.

The method can further comprise:
(g) shifting a head of the dental articulator carrying the upper metal bracket bar vertically relative to a base of the dental articulator carrying the lower bracket bar, and locking the head in an adjusted vertical position;
(h) tilting the upper metal bracket bar about a horizontal axis relative to the head; and
(i) swinging the upper metal bracket bar about an axis perpendicular to the horizontal axis and against a spring force.

The dental articulator which is used in the method thus preferably comprises:
a base;
a post extending upwardly from the base;
a head vertically adjustable on the post;
a lower metal bracket bar on the base projecting forwardly therefrom and provided with upwardly directed formations;
a lower disposable plastic holder formed with a plate provided with formations interfitting with the formations of the lower bracket bar and engageable therewith, and a tongue projecting forwardly from the plate and adapted to be embedded in a lower jaw cast;
an upper metal bracket bar projecting forwardly from the head and provided with upwardly directed formations;
an upper disposable plastic holder formed with a plate provided with formations interfitting with the formations of the upper bracket bar and engageable therewith, and a tongue projecting forwardly from the plate and adapted to be embedded in an upper jaw cast; and
means in the head enabling pivotal movement of the upper metal bracket bar about a horizontal axis and movement of the horizontal axis in a horizontal plane relative to the head.

The means in the head can include:
a lug extending rearwardly from the upper bracket bar into the head;
a pin extending transversely from an end of the lug in the head and defining the horizontal axis; and
spring means in the head biasing the pin toward a position perpendicular to a vertical median plane and the lug toward the median plane.

BRIEF DESCRIPTION OF THE DRAWING

The above and other objects, features, and advantages will become more readily apparent from the following description, reference being made to the accompanying drawing in which:

FIG. 4A is a cross sectional view of the telescoping tube of the articulator of FIG. 4 showing the head from the side;

FIG. 4B is a side elevational view of the head and the inner member of the post seen in section in FIG. 4A;

SPECIFIC DESCRIPTION

Figure 1:
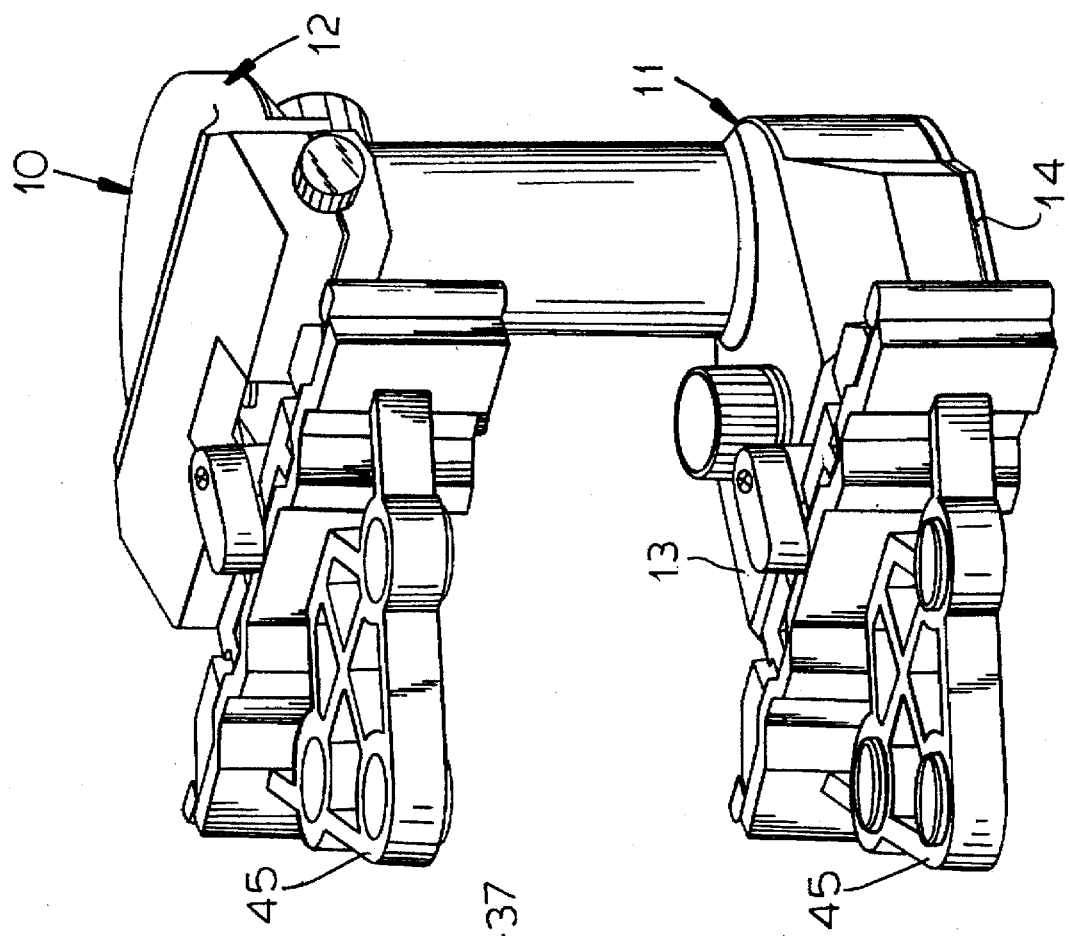
FIG. 1 is a highly diagrammatic view of a dental articulator according to the invention in which both the upper and lower holders are movable.
Figure 2:
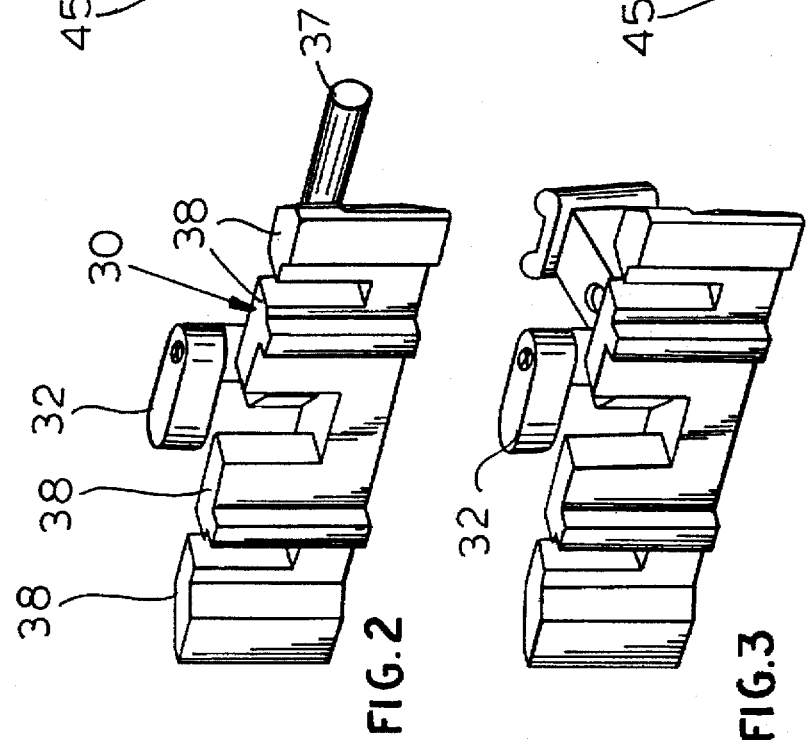
FIG. 2 is a highly diagrammatic perspective view of an upper bracket bar for use with the holder of FIG. 1.
Figure 3:
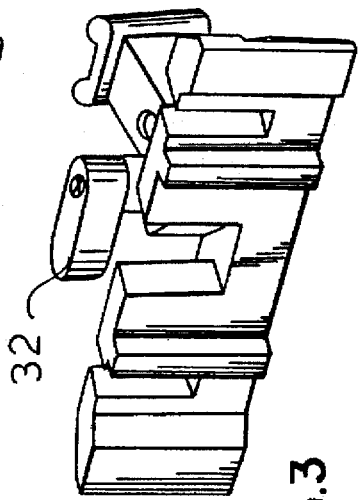
FIG. 3 is a perspective view of a lower bracket bar adapted to be mounted on a base where that bracket bar is not moveable.

Turning to FIGS. 1–4 it can be seen that the articulator 10 comprises a base 11 and a head 12, the base being formed with a downwardly-open cast housing 13 covered by a plate 14 and formed unitarily with an upwardly-extending post 15 which receives a bar 16 anchored to the head 12. As will be apparent from FIGS. 4A and 4B, the post 15 is tubular and receives the bar 16 which can be formed with a channel 17 in which a screw 18 having a milled head 19 can extend. The screw 19 is threaded into the post 15. In operation, the bar 16 can be raised and lowered in the post 15 and the height of the head 12 can be locked by the screw 19.

The base 11 is provided with a bracket bar 20 which can be fixed on the base in one possible embodiment of the invention but normally is articulated thereto to allow movement of the lower dental cast in which a tongue 21 of a holder 22 can be embedded. The holder 22 can be formed with a plate 23 which is contoured to fit onto the bracket bar 20. The bracket bar and holder will be described in greater detail below.

The bracket bar does have an upstanding column 24 provided with a swingable latch 25 which can engage over the plate 23 to retain the holder on the bracket bar. Along the pivot of this holder 25 a screw 26 can be provided which can be tightened to lock the latch 25 in position.

Similarly the bracket bar 30 of the head 12 can be provided with a column 31 and a swingable latch 32 with a locking screw 33 to hold the plate 34 of the holder 35 in place.

Figure 5:
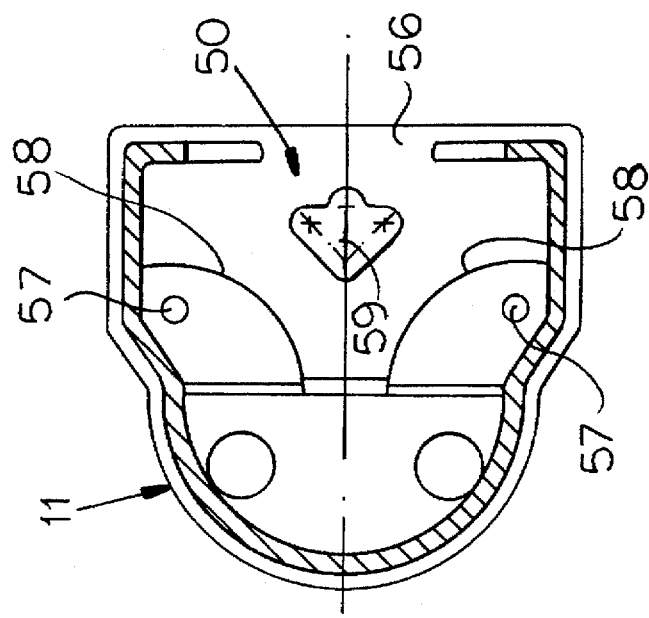
FIG. 5 is a cross sectional view in a horizontal plane through the base of the articulator of FIGS. 1 and 4 with the interior parts removed and the recess on the base plate being seen in plan view.
Figure 5A:
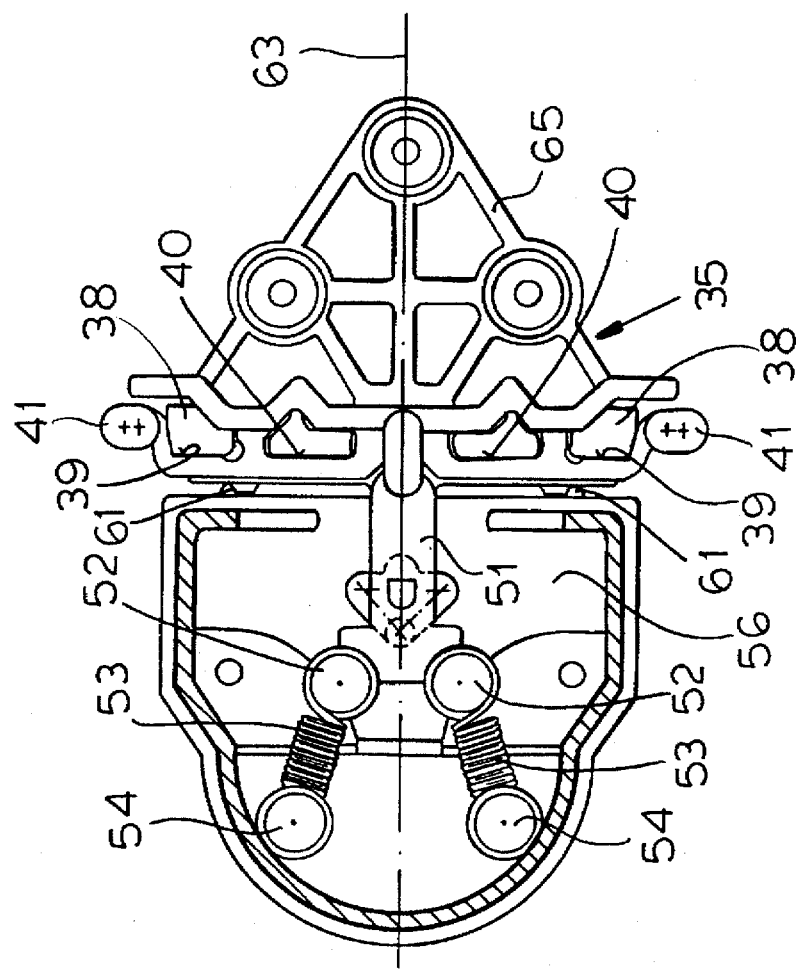
FIG. 5A is a view similar to FIG. 5 showing the lower bracket bar and its spring members in place.

The bracket bar 30 has a rearwardly-extending lug 36 (4A) which is formed within the head 12 with a transverse pin 37 defining a horizontal pivot axis for the bracket bar 30. The bracket bar also has upstanding formations 38 which are received in pockets 39 and 40 of the holder 35 as can be seen in FIG. 5A, the outermost pockets 39 being defined by resilient formations or tongues 41 which hug the outermost projections 38 of the respective bracket bar. It will be apparent that upon rotation of the latches 25 and 32 to clear the plates 23 and 34, the holders can be lifted from or placed upon the respective bracket bar. Each of the holders has a tongue 45, 46, 47 or 48 of an openwork construction as will be described in greater detail hereinafter.

As can be seen in greater detail from FIGS. 5, 5A, 5B and 5C, the base 11 can have a forwardly-open window 50 through which a rearwardly-extending lug 51 of the bracket bar can project and, at its free end, this lug can be provided with two upwardly extending pins 52 which are engaged by eyes of coil tension springs 53. The ends of these springs which are anchored to the housing of the base 11 have eyes engaged over respective pins 54 die-cast unitarily with the housing 55 which is closed at its bottom by a plate 56 connected to the housing 55 by screws threaded into bores 57 of humps 58 also molded unitarily with the housing 55.

The bottom plate 56 has a generally triangular recess 59 which limits the movement of the bracket bar 20. For this purpose, the lug 51 has a downwardly-extending pin 60 engageable in the recess 59.

Figure 5C:
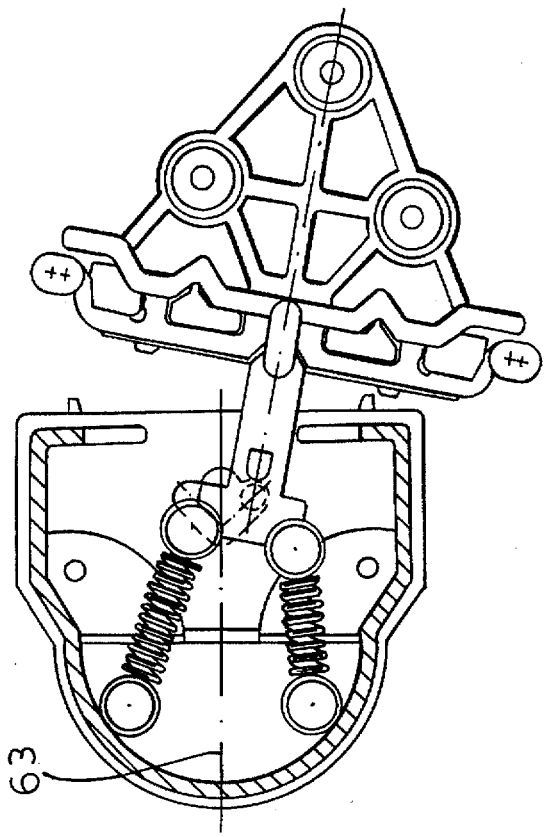
FIG. 5C is another view similar to FIG. 5A showing the holder and bracket bar swiveled to one side of the median plane
Figure 5B:
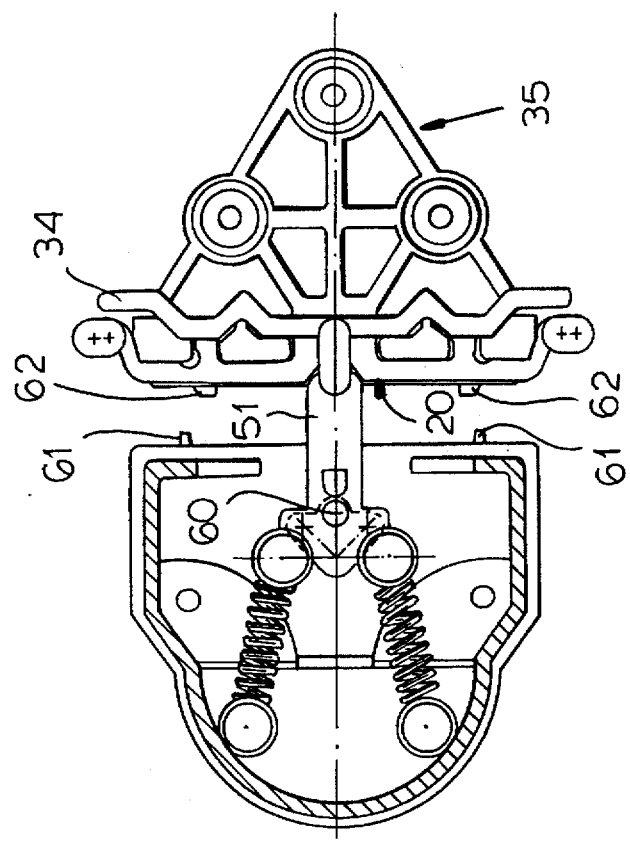
FIG. 5B is a view similar to FIG. 5A but illustrating the bracket bar and its holder in another position.

When the springs 53 are in their most relaxed positions, they draw the lug 51 to the left so that the pin 60 is seated at the vertex of the recess 59 (FIG. 5A). In this position, a pair of projections 61 on the front of the housing 55 can center the bracket bar 20 between them by engagement with projections 62 on the bracket bar (FIG. 5B). When adjustment of the lower holder 35 and the lower jaw casting which is cast on the tongue 45 of this holder is desired, the casting and the lower holder can be drawn to the right from this median position shown in FIG. 5A in which the median plane of the holder lies along the median plane 63 of the base, thereby tensioning the spring and moving the holder 35 into the position shown in FIG. 5B. The holder with the casting thread can be swiveled to either side of the median plane 63 as shown in FIG. 5C.

Figure 6:
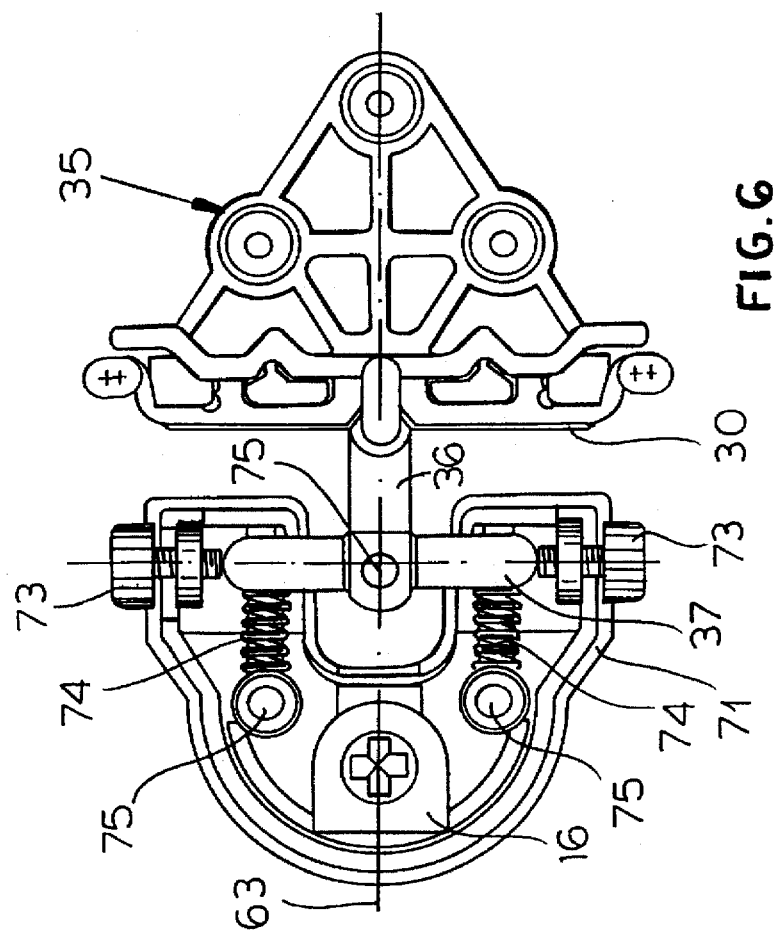
FIG. 6 is a plan view of the head of the articulator with its cover plate removed.
Figure 8:
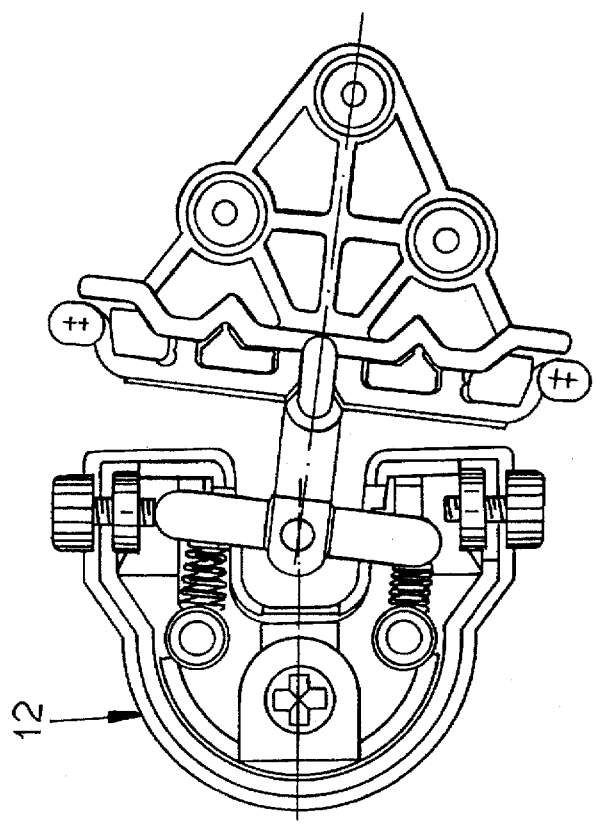
FIG. 8 is another view similar to FIG. 6 with the holder and bracket bar swiveled about the vertical pivot axis of the upper holder.
Figure 7:
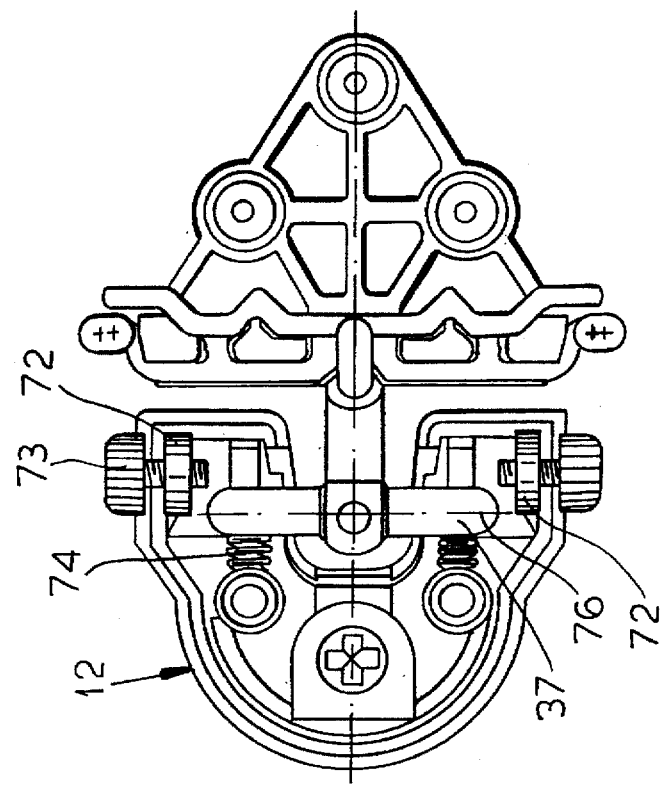
FIG. 7 is a view similar to FIG. 6 but with the upper holder and bracket bar in another position.

The head 12 is shown in FIG. 6–8 with its cover 70 removed from the bottom member 71 which is anchored to the bar 16 previously described. The bottom member 71 is formed with a pair of internally-threaded upwardly-projecting members 72 into which screws 73 with milled heads are threaded. These screws can engage opposite ends of the pin 37 which is anchored to the lug 36 extending toward the housing 70, 71 from the bracket bar 30.

Braced against the pin 37 at its opposite ends are a pair of compression springs 74 anchored on pins 75 die-cast unitarily with the housing 71. The height-adjustment screw 75 extends through the lug 36 to bear against an overhanging part of the cover 70 and thereby allow adjustment of the angular positioning of the upper casting and holder about the horizontal axis 76.

With the springs 74 partly and equally compressed, the bracket bar 30 and the upper holder 35 are biased into the position in which the median plane of the holder is aligned with the median plane 63 of the articulator (FIG. 6). The screws 73 can be tightened against the pin to hold it in place. The screw 75 can then be adjusted to tilt the holder about the axis 37.

Upon loosening of the screws 73, casting and the holder, together with the pin 37 can be forced rearwardly toward the housing (FIG. 7), thereby compressing springs 74. The holder can also be tilted about a vertical axis with differential compression of the two springs (FIG. 8).

The maximum upward tilt of the holder has been shown in FIG. 4B.

Figure 4:
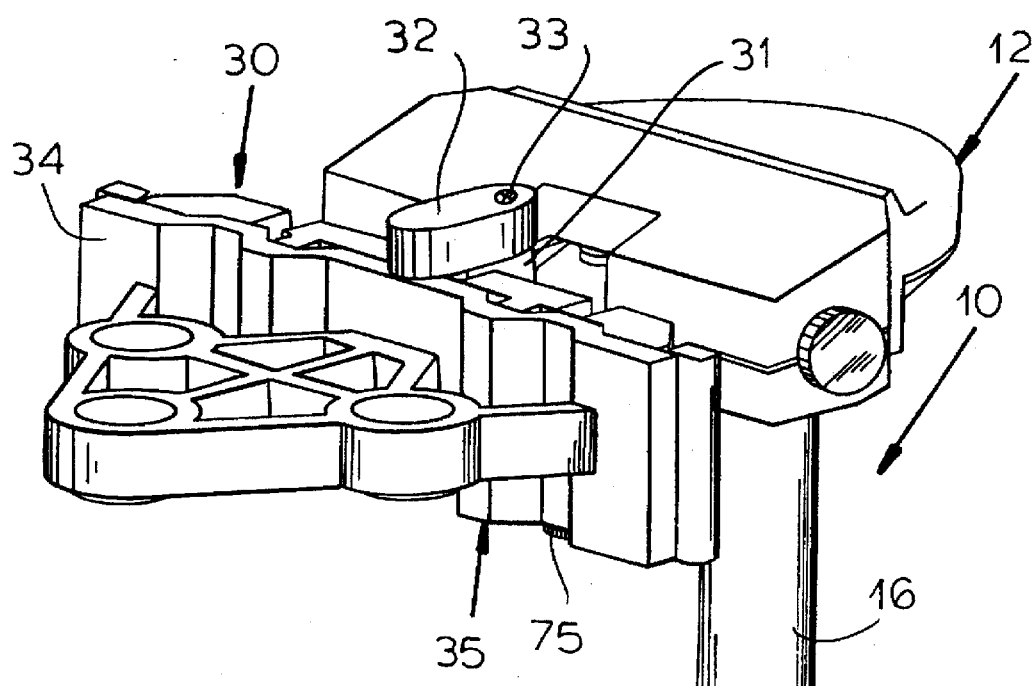
FIG. 4 is a perspective view similar to FIG. 1 but showing the head of the articulator raised relative to the position shown in FIG. 1.
Figure 4:
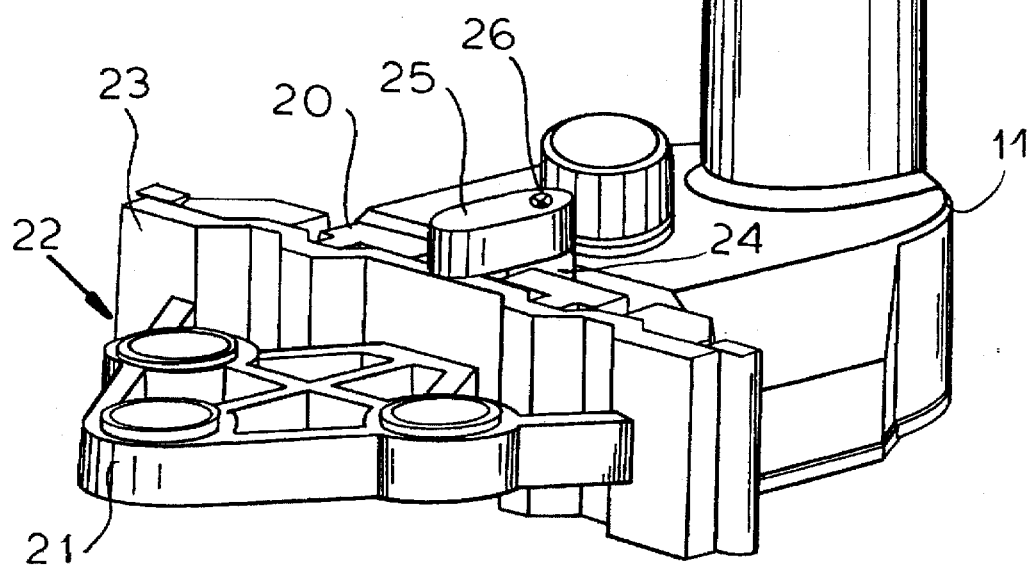
Figure 12:
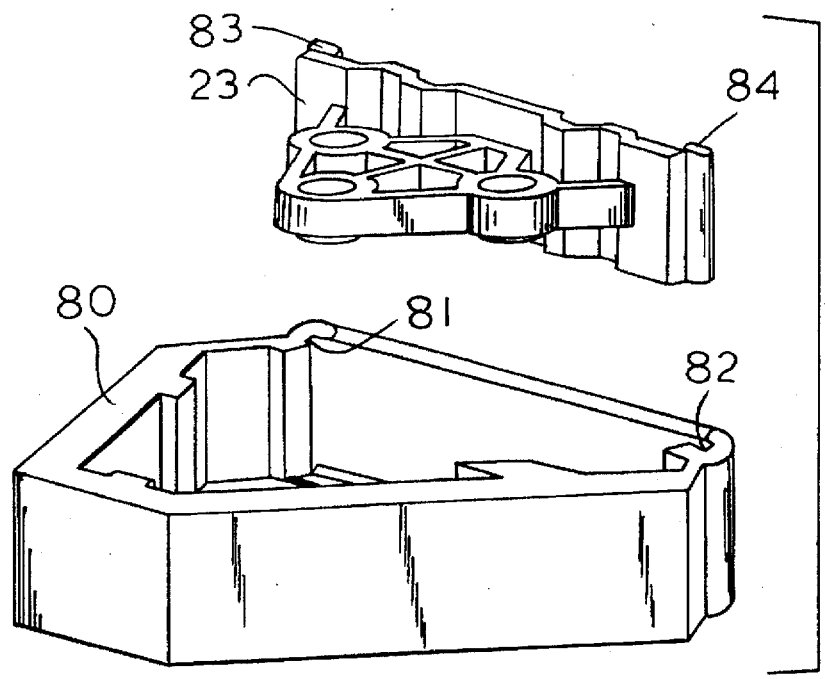
FIG. 12 is an exploded view showing the assembly of a holder into the mold for the lower jaw cast in an exploded perspective view.
Figure 13:
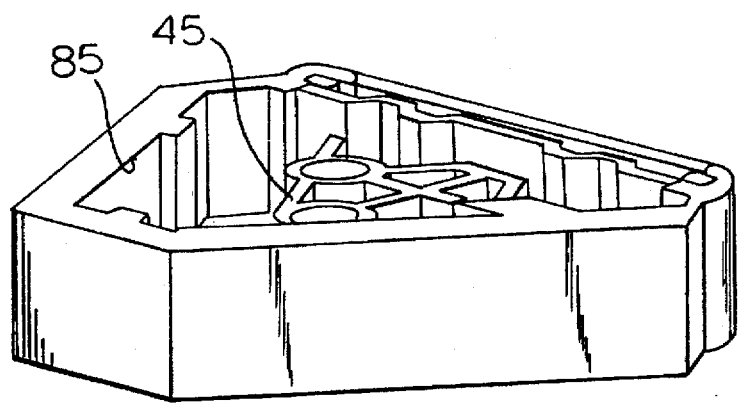
FIG. 13 shows the cast ready to receive the plaster and the tooth bridge.
Figure 14:
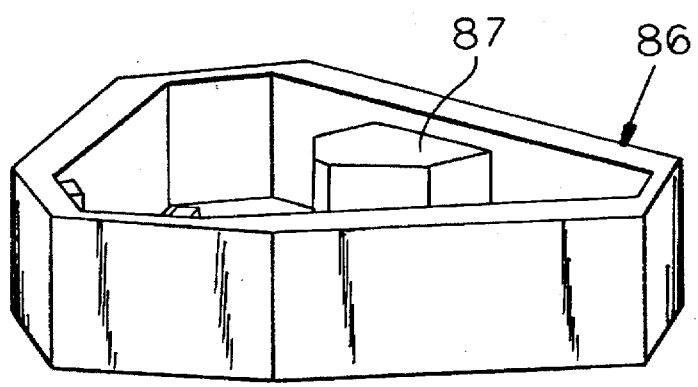
FIG. 14 represents a mold adapted to cast the recess in the upper jaw casting.

Normally the apparatus will include the articulator of FIGS. 1 and 4 and a set of the disposable holders. In addition the apparatus will comprise a mold 80 as can be seen from FIG. 12, which has a pair of vertical guide channels 81, 82 in which the outwardly-projecting edges 83 and 84 of the plate 23 of the lower holder can be guided so that, when the holder is assembled in the mold (FIG. 13), the tongue 45 of the holder is supported in the mold cavity 85 and the tooth mold which has been inserted below the tongue can form the bottom of the mold cavity. The lower jaw casting is then formed by casting plaster therein, thereby embedding the holder in the lower jaw casting.

Figure 15:
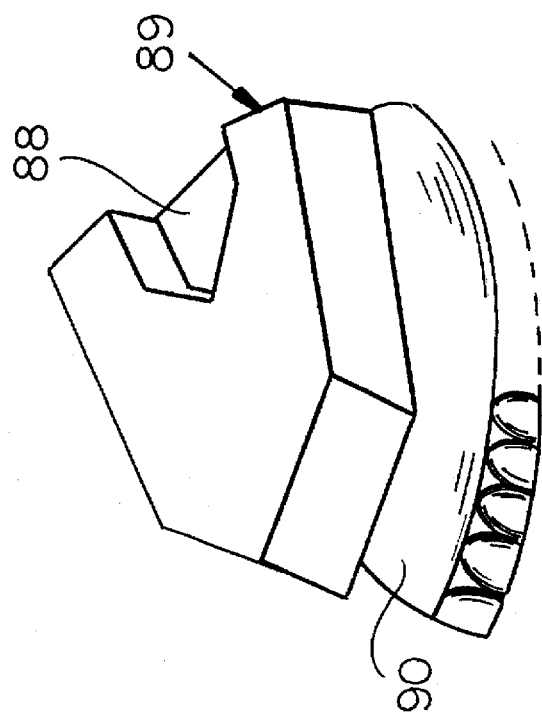
FIG. 15 shows the recess cast in an upper jaw casting to receive the tongue of the respective holder.

The upper casting is formed in another mold 86 forming part of the set, this mold having a projection 87 adapted to form a cavity 88 in the upper jaw casting 89 (FIG. 15) which is formed in this mold. The upper dental arch casting provided on this upper casting as represented at 90 in FIG. 15.

Figure 9:
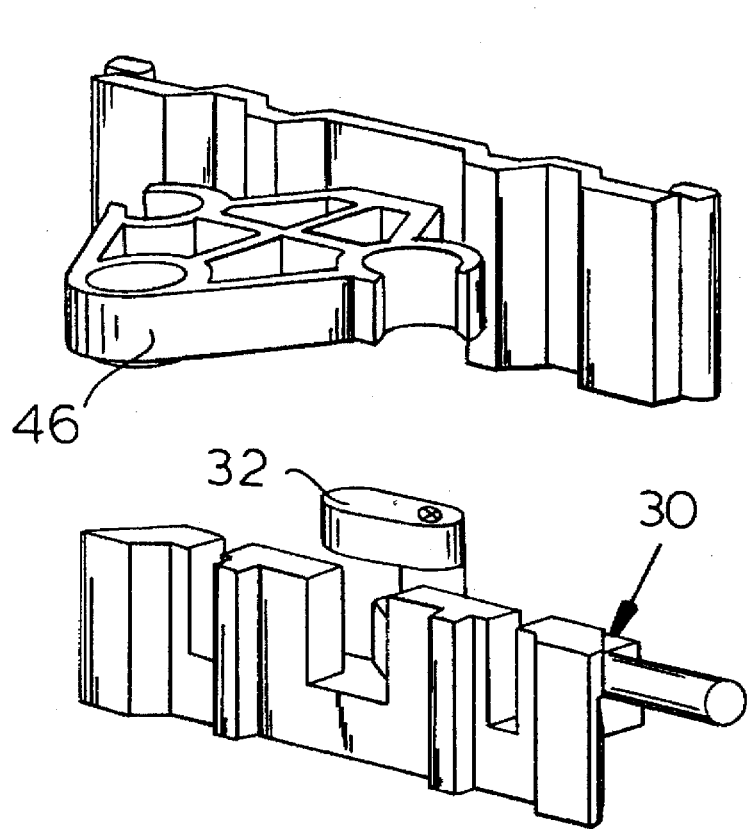
FIG. 9 is an exploded view illustrating the holder separated from the upper bracket bar.
Figure 9A:
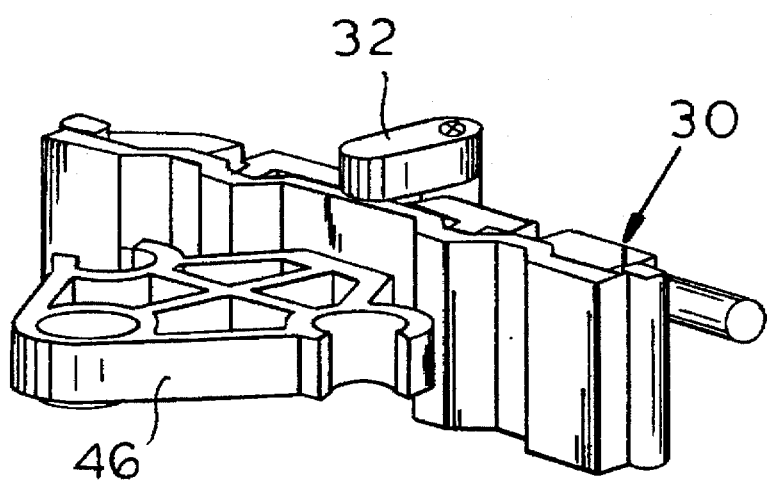
FIG. 9A is a perspective view similar to FIG. 2 representing the assembly of the parts of FIG. 9 with a modified holder tongue.
Figure 10:
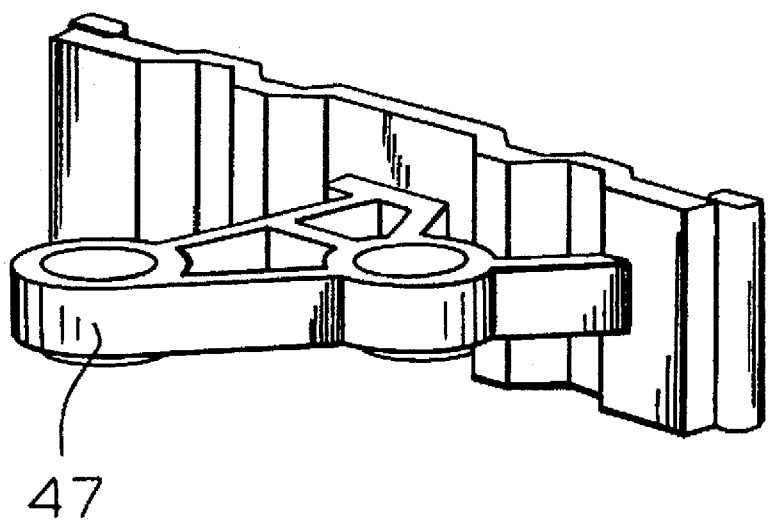
FIG. 10 is a perspective view of another of a set of holders which can be used in the system of the invention.
Figure 11:
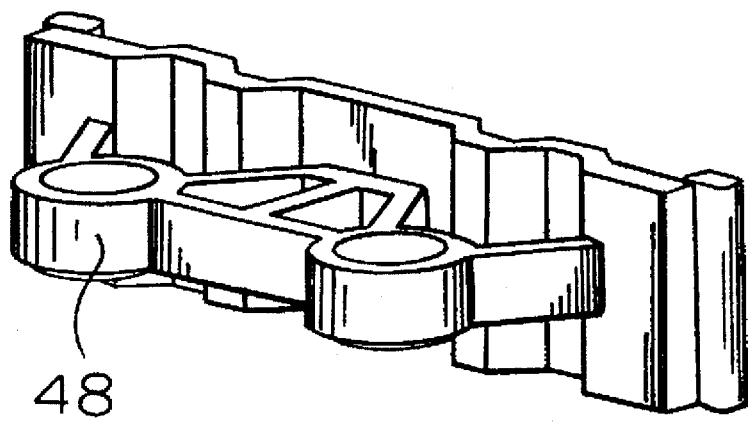
FIG. 11 is a perspective view of still another holder belonging to this set.

In operation, therefore, utilizing the holder embedded in the lower casting, the latter is mounted upon the lower bracket bar 20 in the manner previously described and another holder is mounted on the bracket bar 30 of the head, this holder having its tongue somewhat truncated, e.g. with the configuration shown at 46, 47 and 48 in FIGS. 9–11.

The upper casting is then positioned using the articulator in the manner described in the prior application. Once the casts are in their proper position, the tongue within the cavity 88 is cast in place by plaster introduced into that cavity.

I claim:

1. A method of determining positioning of a lower jaw cast and an upper jaw cast with a dental articulator, the method comprising the steps of:

(a) casting into a lower jaw cast a tongue of a disposable preformed lower plastic holder having a plurality of formations along a plate of the holder from which the tongue projects;

(b) casting an upper jaw cast with an upwardly and rearwardly open recess;

(c) mounting the lower law cast upon a lower metal bracket bar of a dental articulator by sliding the plate of the lower holder over mating formations on the lower metal bracket bar;

(d) mounting on an upper metal bracket bar of the dental articulator a disposable preformed upper plastic holder having a plurality of formations along a plate of the upper holder from which another tongue projects;

(e) positioning the upper jaw cast above the lower jaw cast and in alignment therewith while receiving the other tongue in the recess;

(f) thereafter filling the recess with a hardenable material to embed the other tongue therein and hardening the material to anchor the upper jaw cast to the upper holder and (g) shifting a head of the dental articulator carrying the upper metal bracket bar vertically relative to a base of the dental articulator carrying the lower bracket bar, and locking the head in an adjusted vertical position;

(h) tilting the upper metal bracket bar about a horizontal axis relative to the head; and (i) swinging the upper metal bracket bar about an axis perpendicular to the horizontal axis and against a spring force.

2. The method defined in claim 1, further comprising the step of mounting the lower metal bracket bar on the base for movement in a horizontal plane against a spring force away from the base and to opposite sides of a vertical median plane.

* * * * *